United States Patent [19]

Williams

[11] Patent Number: 4,773,994

[45] Date of Patent: Sep. 27, 1988

[54] LIQUID CHROMATOGRAPHY PACKING MATERIALS

[75] Inventor: Dwight E. Williams, Midland, Mich.

[73] Assignee: Dow Corning Corporation, Midland, Mich.

[21] Appl. No.: 63,147

[22] Filed: Jun. 17, 1987

[51] Int. Cl.$^4$ .............................................. B01D 15/08
[52] U.S. Cl. .............................. 210/198.2; 210/502.1; 210/635; 210/656; 502/401
[58] Field of Search .................... 210/635, 656, 198.2, 210/502.1; 502/401, 402, 403, 404; 530/413, 417

[56] References Cited

U.S. PATENT DOCUMENTS

| | | | |
|---|---|---|---|
| 3,207,699 | 9/1965 | Harding et al. | 252/430 |
| 3,839,395 | 10/1974 | Ostuka | 260/463 |
| 3,960,720 | 6/1976 | Porath | 210/635 |
| 3,984,349 | 10/1976 | Meiller et al. | 252/428 |
| 4,061,503 | 12/1977 | Berger et al. | 106/300 |
| 4,062,693 | 12/1977 | Berger | 106/308 Q |
| 4,105,465 | 8/1978 | Berger | 106/308 Q |
| 4,233,366 | 11/1980 | Sample et al. | 428/405 |
| 4,298,500 | 11/1981 | Abbott | 252/428 |
| 4,324,689 | 4/1982 | Shah | 252/428 |
| 4,379,931 | 4/1983 | Plueddemann | 546/14 |
| 4,539,399 | 9/1985 | Armstrong | 210/502.1 |
| 4,540,486 | 9/1985 | Ramsden | 210/198.2 |
| 4,544,485 | 10/1985 | Pinkerton | 210/502.1 |
| 4,624,932 | 11/1986 | Bogoch | 530/417 |
| 4,675,384 | 6/1987 | Dromard | 530/417 |
| 4,696,745 | 9/1987 | Itagaki | 210/635 |

OTHER PUBLICATIONS

Chang, "High Speed Ion Exchange Chromatography of Protein", Analytical Chemistry, vol. 48, No. 13, Nov. 1976, pp. 1839–1845.

Marshall et al, "Synthesis of LC Reversed Phases of Higher Efficiency by Initial Partial Deactivation of Silica Surface," Journal of Chromatographic Science, vol. 22, Jun. 1984, pp. 217–220.

Pfannkoch et al, "Characterization of Some Commercial High Performance Size-Exclusion Chromatography Columns for Water-Soluble Polymers", Journal of Chromatographic Science, vol. 18, Sep. 1980, pp. 430–441.

Kirkland, J., "High Speed Liquid-Partition Chromatography with Chemically Bonded Organic Stationary Phases," Journal of Chromatographic Science, vol. 9, Apr. 1971, pp. 206–214.

Regnier et al, "Glycerolpropylsilane Bonded Phases in the Steric Exclusion Chromatography of Biological Macromolecules," Journal of Chromatographic Science, vol. 14, Jul. 1976, pp. 316–320.

Poole, C. F., Recent Advances in Silylation of Organic Compounds for Gas Chromatography, Chap. 4, King, Heyder, London 1977, pp. 152–200.

Hertl et al, J. Phys. Chem., vol. 75, No. 14, 1971.

Chmielowiec et al, J. of Coll. & Int. Sci., vol. 9, No. 2, Aug. 1983.

Boksanyi et al, Advance in Coll. & Int. Sci., vol. 6 (1976), pp. 95–132.

Snyder et al, Intro. to Modern Liq. Chrom., 2 ed. Wiley Interscience, N.Y. 1979, pp. 272–279.

Hunnicutt et al, "Reactivity of Organosilane Reagents on Microparticulate Silica", Anal. Chem., vol. 58, 1986, pp. 748–752.

Primary Examiner—Ernest G. Therkorn
Attorney, Agent, or Firm—Killworth, Gottman, Hagan & Schaeff

[57] ABSTRACT

Packing materials for use in liquid chromatographic analysis are prepared by contacting a porous support, such as porous silica, with a ketal silane to form ketal blocked diol groups on the surfaces thereof. An endcapping reagent such as a trimethylsilyl reagent may be added. In addition, the ketal blocked diol groups may be further hydrolyzed to diol groups.

5 Claims, No Drawings

LIQUID CHROMATOGRAPHY PACKING MATERIALS

CROSS-REFERENCE TO RELATED APPLICATION

This application is related to my application Ser. No. 63,576, filed on an even date herewith, and entitled "Liquid Chromatography Dual Zone Packing Material and Method for Making and Using Same."

BACKGROUND OF THE INVENTION

The present invention relates to liquid chromatography packing materials, and more particularly it relates to an improved packing material for use in high performance liquid chromatography and to a method for making and using such a packing material.

The application of modern liquid chromatographic techniques by high performance liquid chromatography (HPLC) has led to an improvement of separation, characterization, and purification of proteins. The separations are based on native properties of the proteins like size (or molecular weight), charge at a given pH and hydrophobicity (originating from amino acid composition and tertiary structure). These differences have been used in classical protein separation procedures as well as with chromatographic techniques. The differences in charge are used in electrophoresis and in ion exchange chromatography. Size differences are utilized in ultra centrifuge separation and in size exclusion chromatography (SEC). The differences in hydrophobicity of the individual proteins have been widely applied in fractionated precipitation by the addition of neutral salts. The chromatographic separation with hydrophobic stationary (reversed) phases has been proven to be a highly effective and versatile tool for protein separation and characterization.

Liquid chromatography using a reverse phase packing has been found to be an effective tool in both qualitative and quantitative analysis for drug substances in blood, serum, or plasma. Typically the reverse phase packing material is made up of bonded alkyl silica and most typically the packing is a porous silica having octadecylsilane (ODS) bonded to it.

Work has recently been done on improving the efficiency of ODS bonded silica packings. See, for example, Marshall et al, "Synthesis of L C Reversed Phases of Higher Efficiency by Initial Partial Deactivation of the Silica Surface," *Journal of Chromatography Science*, Vol. 22., June 1984, pp. 217–220, where it is suggested that pretreating silica with a small amount of end-capping reagent (such as trimethylchlorosilane), followed by exhaustive octadecylation, yields reverse phase packings of higher efficiency (narrower band widths).

Although the efficiency of such packing materials is good, they have a limited life. While ODS packings absorb the lipophilic drug substances from the sample, they also absorb proteinaceous substances which tend to interfere with fractionation of the drug substance from other materials contained in the sample. This eventually leads to a complete fouling of the chromatographic column. Therefore, it has previously been necessary to carry out a preliminary sample preparation procedure to remove the troublesome proteins.

In the most conventional way, the proteins are precipitated, the aqueous supernatant is extracted with a water-immiscible organic solvent, the organic solvent is removed from the extract by evaporation, and the analyte residue is reconstituted in mobile phase before analysis by high-pressure liquid chromatography (HPLC). This method is very time-consuming and cost-inefficient.

A second method currently employed involves the adsorption of analytes onto a reverse phase packing of octadecylsilane bonded to silica in a small disposable column. Although this technique can be automated, the columns can be used for only one sample because proteins remain on the packing, and as a result the technique is also cost-inefficient for multiple samples.

In a third method, a reverse phase packing of octadecylsilane bonded to silica is introduced into a precolumn, which is separated from, but connectable to, an analytical column by a switching valve arrangement. Serum samples are injected directly into the precolumn, where the proteins are denatured and accumulated, and the deproteinated analyte solution is passed into the analytical column for fractionation. After approximately three injections, the precolumn must be backflushed to remove the protein residue. This interruptive backflush is time-inefficient for a large number of samples. Furthermore, the octadecylsilane packing eventually deteriorates because proteins cannot be completely removed therefrom.

Accordingly, for reverse phase liquid chromatography it would be desirable to have a packing material which is less protein adsorptive.

From the standpoint of size exclusion chromatography, it would be desirable to have a packing material wherein the hydrophilic bonded phase forms a dense saturated coverage of the surface, but does not form multiple polymeric layers ("multilayers"). Commercial high performance size-exclusion chromatography columns typically have packing materials comprising a porous silica support with a diol bonded phase, most typically glycerylpropylsilane. See, e.g., Pfannkoch et al, "Characterization of Some Commercial High Performance Size-Exclusion Chromatography Columns for Water-Soluble Polymers", *Journal of Chromatographic Science*, Vol. 18, September 1980, pp. 430–441. However, diol bonded phases tend to provide a thick, multilayered coverage when deposited from aqueous solutions.

It is known that thick multilayered bonded phases show decreased access by solutes and therefore decreased efficiency. See, e.g., Kirkland, J. "High Speed Liquid-Partition Chromatography With Chemically Bonded Organic Stationary Phases," *Journal of Chromatographic Science*, Vol. 9, April 1971, pp. 206–214. For that reason, typically the diol bonded phase is applied to the porous silica support under conditions in which less than saturating amounts are immobilized on the surface, typically in amounts of less than 1.0 molecules per square nanometer (i.e. $\leq 1.0$ m/nM$^2$). See, Regnier et al, "Glycerolpropylsilane Bonded Phases in the Steric Exclusion Chromatography of Biological Macromolecules", *Journal of Chromatographic Science*, Vol. 14, July 1976, pp. 316–320. However, such "light" applications result in a sparce bonded phase which can also lead to column inefficiency.

Accordingly, the need also exists for a size exclusion chromatography packing material with a dense but not multilayered diol bonded phase.

SUMMARY OF THE INVENTION

The present invention meets these needs by providing a packing material which in one embodiment is less protein adsorptive and therefore is an improved reverse phase packing material and in another embodiment provides a dense but not multilayered diol bonded phase and therefore is an improved size exclusion chromatography packing material.

The preferred process for producing the packing materials of the present invention involves the following steps:

(1) A hydroxyl-bearing porous support, such as a porous silica, is contacted with a ketal silane having the formula

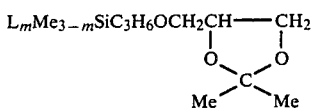

wherein L is chloro, a substituted amino or N-methylacetamido, Me is methyl (i.e. $CH_3$) and m is 1–3. Preferably the ketal silane is

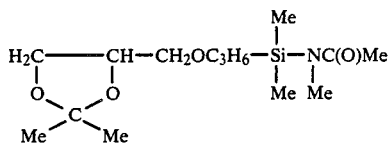

(2) Optionally, an end-capping reagent, such as a trimethylsilyl reagent, may then be used to end-cap the remaining hydroxyl groups (silanols) on both the internal and external surfaces of the support.

The result of steps 1 and 2 is a packing material which may be used in reverse phase liquid chromatography. It has a ketal blocked diol (KBD) on both the internal and external surfaces of the porous support. Such ketal blocked diol groups have portions which are lipophobic in nature and are relatively less adsorptive to proteins. Other portions of the porous support are lipophilic in nature and serve as a lipophilic partitioning phase, probably due to the presence of the dimethyl groups and/or the alkyl chain of the ketal silane. The nature of the lipophilic portions of the porous support give it reverse phase properties sufficient to separate and quantify many small molecules (e.g. drugs) in protein-containing biological substances (e.g. blood serum or plasma).

If the optional end-capping step is undertaken, both the internal surface and the external surface of the porous support will have trimethylsilyl end-capping groups thereon. Such end-capping groups are relatively less adsorptive and as such are preferable to the hydroxyl groups of the porous support which might otherwise remain unreacted.

As a further optional step, other reverse phase surface treatments may be used in combination with the ketal blocked diol groups of step 1. Thus, it is possible to pretreat the porous silica to form other groups, for example, octadecylsilyl (ODS) groups in less than saturating amounts, on the surfaces of the porous silica. A combination of ODS and KBD groups on the surfaces of the porous silica provides a reverse phase packing material useful in instances where it is desirable to reduce the adsorption of the packing to between that of a saturated ODS surface and that of a saturated KBD surface. Optionally, the ketal groups of such packings may be hydrolyzed to the diol to improve column retention stability and further reduce reverse phase adsorption to a desired level. Similarly other combinations reverse phase treatments may be used along with the ketal blocked diol.

In any event, the reverse phase packing material of the present invention has been shown to display a reduced degree of serum protein adsorption because the external surface of the packing material contains ketal blocked diol groups which are less adsorptive to the proteins. The proteins pass through a column packed with the reverse phase packing materials of the present invention while small molecules, such as drugs and metabolites, are separated by the lipophilic partitioning phase.

While the reverse phase packing materials of the present invention are generally not as effective as the dual zone reverse phase packing materials of copending application Ser. No. 63,576, they have been found to operate satisfactorily in most instances. And yet, the process for producing the reverse phase packing materials of the present invention is less complex than that disclosed in copending application Ser. No. 63,576.

Should a packing material having a diol bonded phase useful for size exclusion chromatography be desired, then a third step may be performed. In the third step, the ketal blocked diol groups are (3) hydrolyzed, with for example $H_2SO_4$, to cleave the ketal groups and form diol groups, such as

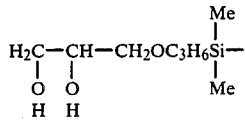

on the surfaces of the porous support.

By doing so, a dense diol bonded phase is created, but it is not a multilayered one. It has greater ability to prevent column inefficiency than sparce "light" diol bonded phases and it also has greater access to solutes than thick multilayered diol bonded phases.

Accordingly, it is an object of the present invention to provide a packing material having either improved reverse phase chromatography characteristics or having improved size exclusion chromatography characteristics, to provide a method for making such packing materials, and to provide a method for using the improved packing materials of the present invention. Other objects and advantages advantages of the invention will become apparent from the invention will become apparent from the following detailed description of the appended claims.

DETAILED DESCRIPTION OF THE PREFERRED EMBODIMENT

The porous support for the packing materials of the present invention may be any porous solid having hydroxyl groups on its surface such as porous metalloid oxides, porous metallic oxides, and porous mixed metallic oxides. Such materials include silica, silica gel, alumina, stannia, titania, zirconia, and the like. However, normal HPLC packings are almost always silica particles or silica gels and therefore porous silica is the most preferred. Accordingly, the porous support will hereinafter be referred to as a porous silica. Preferably the pore diameter is 50 to 120 angstroms and most preferably around 60 angstroms for a reverse phase packing material and 50 to 1000 angstroms and most preferably around 300 angstroms for an SEC packing material.

As mentioned, the first step in the production of the packing materials of the present invention is contacting the porous silica with a ketal silane having the formula

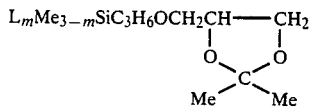

wherein L is chloro, a substituted amino or N-methylacetamido, Me is methyl, and m is 1–3. The preferred ketal silane is

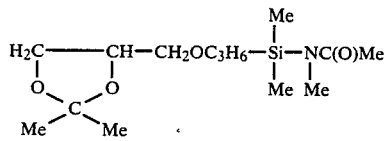

Ketal silanes of this type may be prepared by the method disclosed in copending application Ser. No. 914,899, filed Oct. 3, 1986, and assigned to the same assignee as the present invention. The disclosure of that copending application is hereby specifically incorporated by reference.

The N-methylacetamide group found on the preferred ketal silane is one of the "leaving groups" disclosed in copending application Ser. No. 901,349, filed Aug. 28, 1986, and assigned to the same assignee as the present invention, the disclosure of which is also hereby incorporated by reference. Accordingly, the ketal silane containing the N-methylacetamide leaving group can be considered a "rapidly reacting" silane. As disclosed in application Ser. No. 901,349, rapidly reacting silanes of this nature react first primarily with hydroxyl groups on the external surface of the porous support; however, under the conditions encountered in the present invention, both the external and internal surfaces will have ketal blocked diol groups thereon.

The ketal silane may be used in an amount ranging from 0.5 to 10.0 m/nM² and preferably 1.7 to 4.8 m/nM² and most preferably the porous silica is contacted with an amount of about 2.4 n/nM² of the preferred ketal silane in a dry non-protic solvent at reflux for a preferred time of 1 to 16 hours. This will result in the surfaces of the porous support having ketal blocked diol (KBD) groups thereon.

At this stage, a number of silanols may remain unreacted on both the internal surface and external surface of the porous silica. Therefore, as an optional step, an end-capping reagent may be added to convert any undesirable residual silanols to less adsorptive trimethylsilyl (TMS) groups. This is preferably done by contacting the porous silica with an excess of $((CH_3)_3 Si)_2 NH$, e.g. 2.0 m/nM². This should be done for a sufficient period of time to assure complete treatment of the accessible remaining silanols. As mentioned, this step is optional and may be omitted. In either event the packing material at this stage is usable in reverse phase chromatography.

Another optional step is hydrolysis with, for example, 0.5 molar $H_2SO_4$ at room temperature for about 6 hours to cleave the ketal blocked diol groups and form diol groups. Thus, using the preferred ketal silane, and following hydrolysis, the diol groups would be

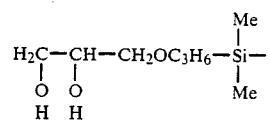

Such a diol bonded phase renders the packing useable in size exclusion chromatography.

EXAMPLE

Preparation of a reverse phase packing material

Initially 5.00 g of ICN/Woelm silica (surface area 424 m²/g., particle size 5 um) (preweighed, dried at 180° C. in a vacuum oven for 16 hours) and 200 cc hexane (dried over molecular sieves and filtered) were placed in a 500 cc, three-necked, greaseless baffled flask equipped with a $N_2$ sweep and the slurry sonicated 10 minutes to displace air from the pores of the silica. The flask was then equipped with an air-motor driven paddle, addition funnel, and a condenser topped with a drierite-protected $N_2$ sweep to exclude moisture during reaction. The mixture was stirred and heated for 20 minutes until the reaction is at reflux. Next, 5.7 cc of a ketal silane in 20 cc hexane was added at reflux over 5 minutes. The structure of the ketal silane was

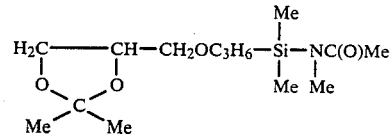

and was denoted KBDA. After addition of the KBDA, 20 cc hexane rinse was added all at once. The mixture was refluxed for 2 hours. Then the mixture was allowed to cool to room temperature without stirring and the treated silica was isolated by filtration and cleaned by successive washings, twice with hexane, once with ethanol, and thrice with diethyl ether. The treated silica was dried in a vacuum oven overnight at 80° C. The treated silica gave a bulk analysis of 12.58 WT% C.

The treated silica was, then, packed in a chromatographic column (4.6 mm × 100 mm), and attached to a Perkin Elmer 2C-55 Spec. A sample of benzyl alcohol in 0.1 molar $H_3PO_4$ buffer in a 5 ul sample loop, at 1 ml/min flow was analyzed. The benzyl alcohol was detected at a k' of 2.4, a considerable increase over the diol bonded phases of the prior art.

Having described the invention in detail and by reference to the preferred embodiment thereof, it will be apparent that modifications and variations are possible without departing from the scope of the invention defined in the appended claims.

What is claimed is:

1. A reverse phase packing material for liquid chromatographic columns which comprises a porous support having ketal blocked diol groups on the surfaces thereof wherein said ketal blocked diol groups have the formula:

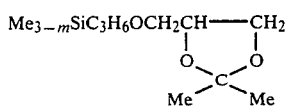

wherein m is 1–3.

2. The packing material of claim 1 wherein said porous support is porous silica.

3. The packing material of claim 2 wherein said ketal blocked diol groups have the formula

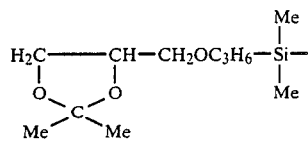

4. The packing material of claim 3 wherein said porous silica support also has trimethylsilyl end-capping groups on the surfaces thereof.

5. The packing material of claim 3 wherein said porous silica support also has octadecylsilyl groups on the surfaces thereof.

* * * * *